US00RE35849E

United States Patent [19]

Soehendra

[11] E Patent Number: Re. 35,849

[45] Reissued Date of Patent: Jul. 14, 1998

[54] INDWELLING STENT

[75] Inventor: Nib Soehendra, Norderstedt, Germany

[73] Assignee: Wilson-Cook Medical, Inc., Winston-Salem, N.C.

[21] Appl. No.: 367,801

[22] Filed: Dec. 30, 1994

Related U.S. Patent Documents

Reissue of:

[64] Patent No.: 5,176,626
Issued: Jan. 5, 1993
Appl. No.: 821,001
Filed: Jan. 15, 1992

[51] Int. Cl.[6] ..... A61M 25/00

[52] U.S. Cl. ..... 604/8; 604/9; 604/286

[58] Field of Search ..... 604/8, 9, 10, 11, 604/19, 27, 43, 48, 93, 264, 286

[56] References Cited

U.S. PATENT DOCUMENTS

| | | | |
|---|---|---|---|
| 3,690,323 | 9/1972 | Wortman et al. | |
| 3,938,529 | 2/1976 | Gibbons | 128/349 |
| 4,382,445 | 5/1983 | Sommers | 604/8 |
| 4,474,569 | 10/1984 | Newkirk | 604/8 |
| 4,671,795 | 6/1987 | Mulchin | 604/8 |
| 4,767,400 | 8/1988 | Miller et al. | 604/8 |
| 4,913,683 | 4/1990 | Gregory | 604/8 |
| 4,955,859 | 9/1990 | Zilber . | |
| 4,973,301 | 11/1990 | Nissenkorn | 604/8 |
| 5,019,102 | 5/1991 | Hoene | 604/281 |
| 5,052,998 | 10/1991 | Zimmon | 604/8 |
| 5,059,169 | 10/1991 | Zilber | 604/8 |
| 5,167,614 | 12/1992 | Tessman et al. | 604/8 |

*Primary Examiner*—Sam Rimell
*Attorney, Agent, or Firm*—Woodard, Emhardt, Naughton, Moriarty & McNett

[57] ABSTRACT

An indwelling stent is disclosed which facilitates the drainage of fluids through a duct within the body, and which is easily removed when needed. The disclosed stent is a double wing stent and includes multiple flaps at each end for anchoring and has a continuously uninterrupted drainage tube therebetween. Constructed at the outflow end of the stent is a wick, which is made of an extended arcical section of the drainage tube of the stent and serves to enhance drainage by providing a "wicking" effect for fluid as it exits the stent's outflow end, while inhibiting reflux by allowing for the sphincter at the exit of the obstructed duct to function in a normal manner. The wick further serves to facilitate removal by providing a portion which is easily graspable by an instrument inserted into the body for retention and removal.

18 Claims, 3 Drawing Sheets

INDWELLING STENT

Matter enclosed in heavy brackets [ ] appears in the original patent but forms no part of this reissue specification; matter printed in italics indicates the additions made by reissue.

BACKGROUND OF THE INVENTION

1. Field of the Invention

The field of the invention is indwelling stents which aid in the drainage of fluids within the body.

2. Description of the Prior Art

A number of various stents have been devised which are designed to aid in the drainage of fluids within the body. It is generally desirable that a stent being implanted for this purpose be easily implantable, that it maintain patency of the duct and its position within the duct after implantation, that reflux or backflow through the duct be avoided, and that the stent be easily removable.

Stents have been designed in a wide variety of shapes and sizes to effectuate these general requirements. One such example is shown by U.S. Pat. No. 5,052,998 to Zimmon which discloses an indwelling stent having flaps at its inflow end and a pigtail configuration at its outflow end to facilitate anchoring of the stent within the duct to be drained, and also has a series of drainage holes along its length to facilitate drainage. Other stents mentioned in the Zimmon patent, have commonly employed double flaps, or wings, or have incorporated pigtails on both ends, to hold the stent in place. Prior art stents have been provided both with and without the drainage holes shown in the Zimmon patent.

Reflux is the condition where fluids and/or debris are drawn backwardly up into the duct to be drained. This is undesirable in that it is counterproductive to the purpose of the stent being implanted to drain the duct. Reflux of debris into the stent can also potentially occlude the implanted stent within the duct, which can potentially cause severe aggravation to the condition being treated. Reflux is normally prevented by the functioning of a sphincter located where the duct exits into its receiving organ, however this sphincter operation is inhibited by the placement of an indwelling stent which acts to maintain the patency of the sphincter as well as the duct being drained.

To prevent reflux, U.S. Pat. No. 5,019,102 to Hoene discloses a stent with a dynamic hood-valve at the vesical end of the stent, located within the receiving organ at the downflow end of the obstructed duct. The hood-valve is comprised of a hood-shaped plastic foil that is attached to and partially surrounds the vesical end opening. A reflux pressure causes the hood-valve to fold over to close the vesical opening, thereby preventing retrograde flow from occurring.

Some stents have been devised which terminate within the duct to be drained to allow for normal sphincter operation. U.S. Pat. No. 4,955,859 to Zilber is one such example which suggests the use of a ureteral stent which terminates within the urethra to allow for the normal operation of the external sphincter in order to prevent incontinence.

It is known in the prior art to incorporate means for facilitating the removal of an indwelling stent from the body. U.S. Pat. No. 4,671,795 to Mulchin discloses one such example of an indwelling stent which has a suture attached to its end which extends out of the body and is tied to a button outside the body. The button prevents upward migration and may be pulled to remove the stent from the body.

U.S. Pat. No. 4,913,683 to Gregory is another reference disclosing a stent system which utilizes sutures that extend outwardly of the patient and are pulled to remove the stent from the body. Zilber suggests the use of trailing sutures as an aid in the positioning of a stent being implanted. Zimmon suggests drawing the end of a large diameter stent (10 French or greater) to a reduced diameter to facilitate removal [col. 3, lines 52–57] in an effort to compensate for the fact that larger diameter stents are more difficult to grasp and remove.

SUMMARY OF THE INVENTION

The present invention generally provides a new and unique indwelling stent which facilitates the drainage of fluids through a duct within the body. When implanted within an obstructed duct to be drained, a stent according to the present invention acts to enhance drainage while preventing reflux by allowing the sphincter at the exit of the duct to function normally. The stent is also easily removed when needed. According to the preferred embodiment disclosed herein, a double wing stent, having multiple flaps at each end and a continuous uninterrupted drainage tube therebetween, is implantable within an obstructed duct. Located at the outflow end of the drainage tube of the stent is a "wick" which is made of an extended arcical section of the drainage tube.

The stent, when implanted with the outflow end of its drainage tube within the duct, prevents reflux by allowing the sphincter at the exit of the duct to function normally. In this operative position, the wick extends through the remaining section of the duct and into the receiving organ. The wick serves to enhance drainage by providing a "wicking" effect for fluid as it exits the stent's outflow end and, with the outflow end of the drainage tube wholly within the duct, the sphincter at the exit of the duct is allowed to function normally, thereby preventing reflux. In this way, the implanted stent tends to remain unobstructed for longer periods of time and therefore is safer for the patient and may remain in place without the need for replacement for longer periods. The wick further serves to facilitate removal by providing an exposed portion which is easily graspable by an instrument inserted into the body to retain and remove the stent.

It is an object of the present invention to provide an improved stent for the drainage of fluids within the body.

It a further object of the present invention to provide such a stent which facilitates drainage within an obstructed duct while allowing the sphincter at the exit of the duct to function normally to inhibit reflux.

It a further object of the present invention to provide such a stent which is easy to remove when needed.

It is yet another object to provide such a stent which has the advantage of simplicity of construction.

These and other objects and advantages will be apparent from a review of the following specification and claims.

BRIEF DESCRIPTION OF THE DRAWINGS

FIG. 1a is a side elevational view of a stent for facilitating the drainage of fluids within an obstructed duct. FIG. 1b is a top plan view of the stent 10 of FIG. 1a. FIG. 1c is a perspective view of the out flow end of stent 10, while FIGS. 1-d is an end view of the outflow end of this stent.

FIGS. 2a–b show the stent implanted within the duct, with the outflow end of its drainage tube wholly within the duct, and its wick extending through the exit of the duct and into the receiving organ. In FIG. 2a, the sphincter at the exit of the duct is open to allow the free flow of fluid out of the duct and into the receiving organ. In FIG. 2b, the sphincter is closed to prevent the reflux of fluid and/or debris back into the duct.

DESCRIPTION OF THE PREFERRED EMBODIMENT

Figure 1A:
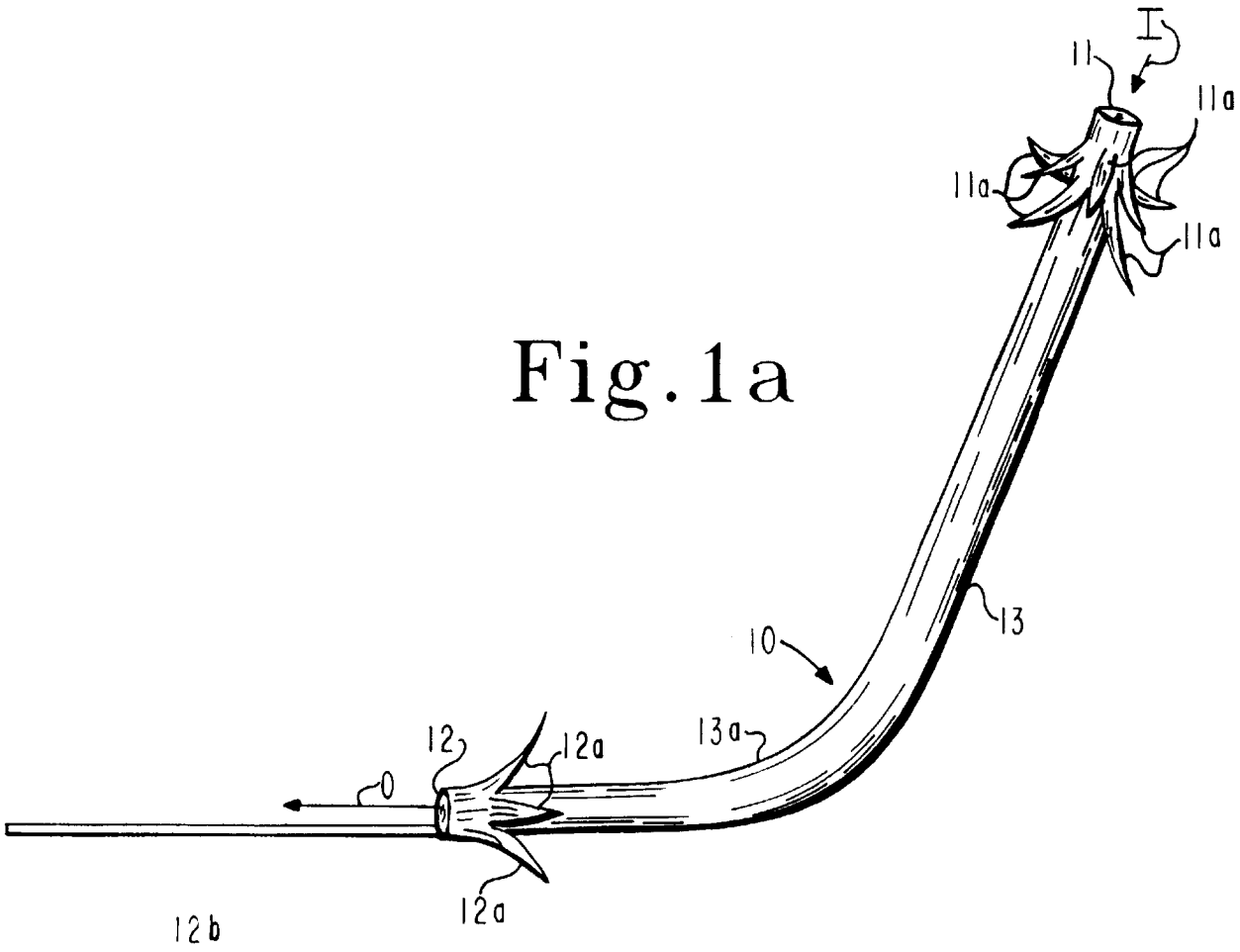
FIGS. 1a–d are various illustrations of a stent according to the present invention.
Figure 1D:
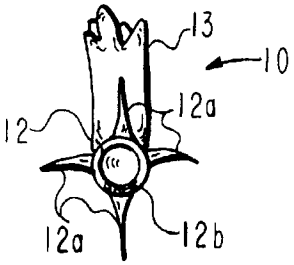
Figure 1C:
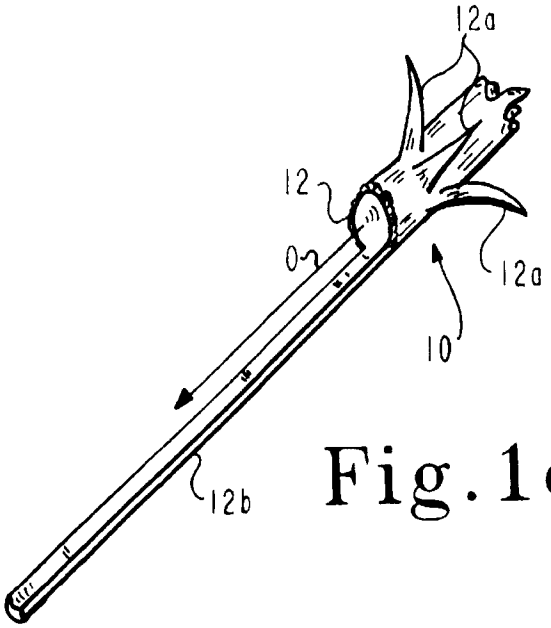
Figure 1B:
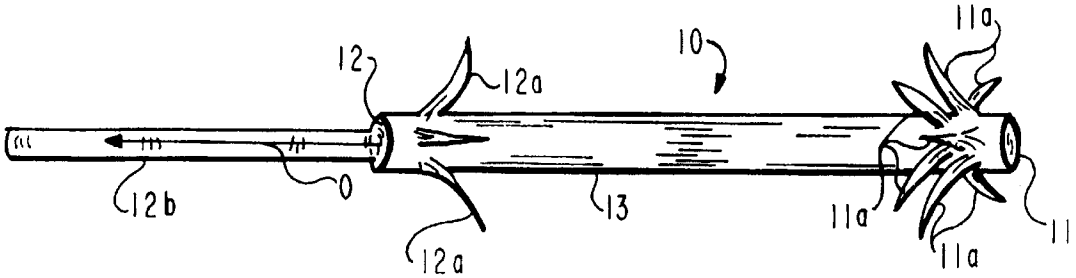

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIGS. 1a–d are various illustrations of a stent of the present invention, which will now be described with reference to these figures. Stent 10 is made of radiopaque polyethylene and has an inflow, end portion 11 and an outflow end portion 12, and a drainage tube 13 therebetween. Inflow end portion 11 defines inlet I for allowing fluid to enter into drainage tube 13, while outflow, end portion 12 defines outlet O for allowing fluid to exit drainage tube 13. At inflow end 11 are two alternating rows of four radially extending flaps 11a which serve to aid in the anchoring of stent 10 within an obstructed duct. In the same manner and for the same purpose, radially extending flaps 12a are located at outflow end portion 12 of stent 10, except that only one row of four flaps 12a, as shown, are incorporated at outflow end portion 12 for the prevention upward migration. The number, size, and orientation of flaps 11a and 12a may be modified to accommodate the mitration-preventing requirements of the particular stent to be implanted.

Flaps 11a and 12a are simply constructed by slicing small longitudinal sections in stent 10 and orienting the sliced sections radially. It is preferred that the above described slices are made shallowly such that holes are not made within the drainage tube by the construction of flaps 11a and 12a.

Drainage tube 13 is comprised of a continuously uninterupted tube and provides a drainage passageway though an obstructed duct when stent 10 has been implanted therein. Drainage tube 13 has a 120° bend 13a at approximately one third of its overall length from outlet O. Bend 13a is incorporated in stent 10 to accommodate the anatomical structure of the duct into which stent 10 is to be implanted, which by this example is the biliary duct.

Wick 12b, located at outflow end 12 of stent 10, is comprised of an extended arcical section of drainage tube 13 and serves to enhance drainage by providing a "wicking" effect for fluid as it exits outlet O. Wick 12b further serves to allow stent 10 to be implanted with its outflow end 12 positioned within duct 20 rather than extending into the receiving organ 30, thereby allowing sphincter 21 at the exit of duct 20 to function normally to prevent reflux. Additionally, wick 12b serves to facilitate removal by providing an exposed portion, extending through sphincter 21 and into receiving organ 30, which is easily graspable by an instrument inserted into the body to retain and remove stent 10.

In the embodiment shown, wick 12b has an arcical cross-section of about 70° which is intended for illustrative purposes. Arcical cross-sections of wider or narrower dimension than specifically disclosed herein may serve to provide the intended and described novel functions of wick 12b and, as such, are considered to fall within the scope of this invention.

Figure 2B:
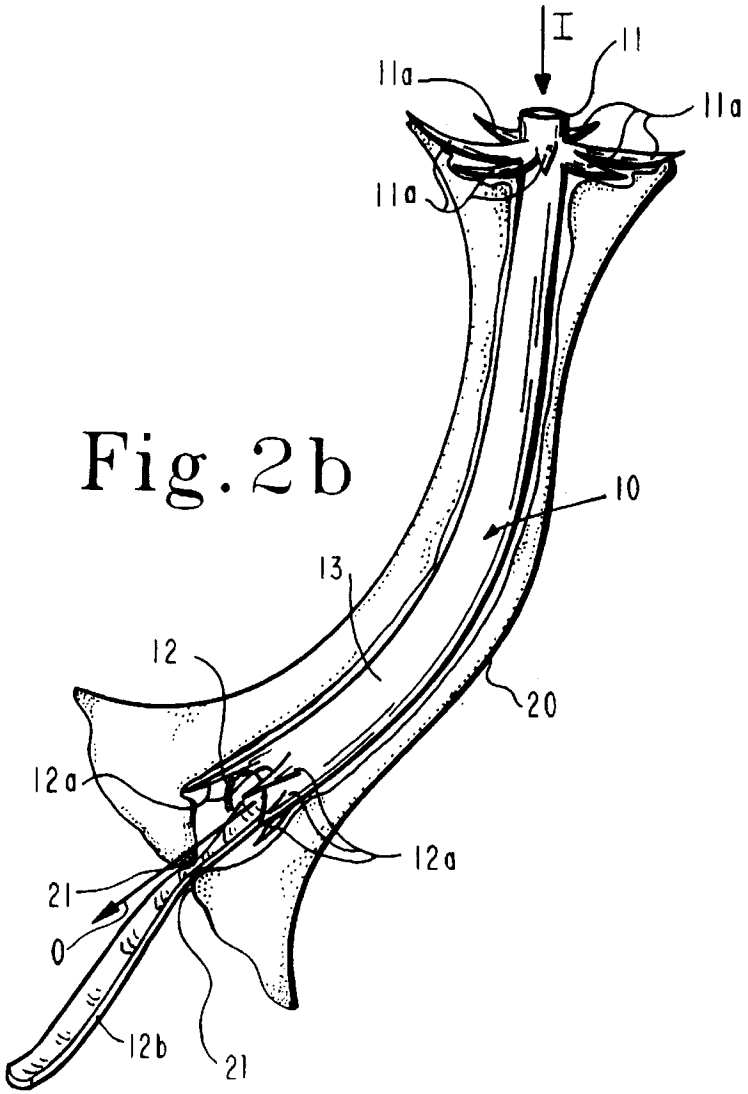
FIGS. 2a–b are illustrations of the stent of FIGS. 1a–d implanted within an obstructed duct to aid in the drainage of fluids therethrough.
Figure 2A:
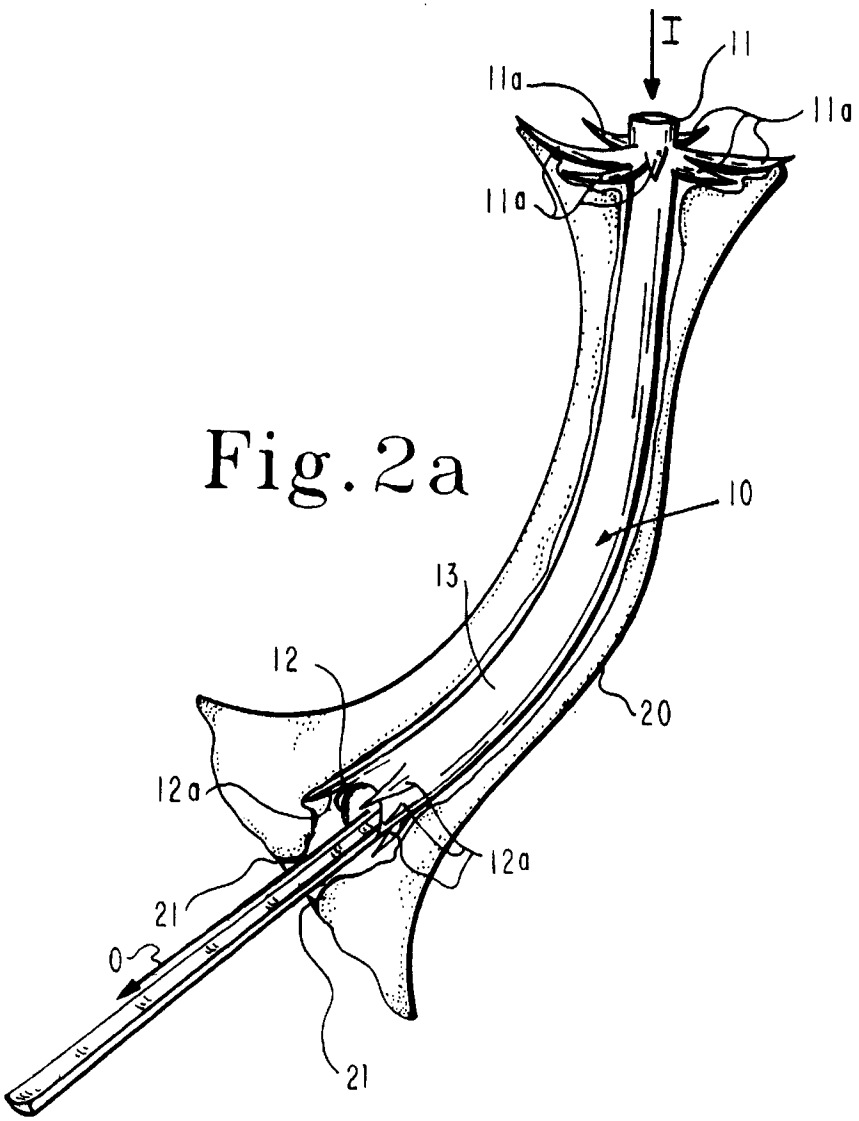

FIGS. 2a–b illustrate the stent of FIGS. 1a–d implanted within an obstructed duct 20 to aid in the drainage of fluids therethrough. When implanted, flaps 11a and 12a serve to anchor stent 10 in place within duct 20 and prevent undesirable migration. Drainage tube 13 maintains patency within duct 20, thereby allowing fluids to flow therethrough. Wick 12b provides a wicking effect which enhances the further flow of fluid upon exiting drainage tube 13 at outlet O, while also allowing sphincter 21 to function normally, thereby serving to reduce the possible occurrence of reflux.

The normal operation of sphincter 21 is illustrated by the comparison of FIGS. 2a and b. In FIG. 2a, sphincter 21 is opened to allow the free flow of fluid away from duct 20. In this state, wick 12b enhances drainage by providing a wicking effect for fluid as it exits the outflow end of drainage tube 13. In FIG. 2b, sphincter 21 is closed to prevent reflux from occurring. In this state, sphincter 21 closes about wick 12b to effectuate closure. When stent 10 is to be removed, wick 12b also serves the function of facilitating such removal by providing an exposed portion which is easily graspable by forceps or other instrument inserted for removal.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A stent for facilitating the drainage of fluids through an obstructed duct within the body and through a sphincter at the exit of the obstructed duct while inhibiting reflux by allowing for the normal functioning of the sphincter, said stent comprising:

an inflow end portion, an outflow end portion, and a drainage tube therebetween, said inflow end portion defining inlet means for allowing fluid to enter into the inflow end of said drainage tube, said outflow end portion defining outlet means for allowing fluid to exit the outflow end of said drainage tube;

means for anchoring said stent in an obstructed duct with the inflow end of said drainage tube positioned within the duct; and means for enhancing the drainage for fluid exiting said outlet means from within the duct while inhibiting reflux by allowing for the sphincter at the exit of the duct to function in a normal manner, said drainage enhancing/reflux inhibiting means including a wick extending from the outflow end of said drainage tube and comprising an extended arcical section of said drainage tube, whereby said wick enhances drainage by providing a wicking effect for fluid exiting said drainage tube while reducing the possible effect of reflux by allowing the sphincter at the exit of the duct to function in a normal manner.

2. The stent of claim 1 in which, when said stent has been implanted in a duct to be drained, said wick extends through the sphincter at the exit of the duct with said sphincter being allowed to function normally by closing about said wick, and further whereby said wick provides means for facilitating removal of said stent by providing an exposed portion of said stent which is easily graspable by an instrument inserted into the body for retention and removal.

3. The stent of claim 1 wherein the arcical cross-section of said wick is about 70°.

4. The stent of claim 1 in which said anchoring means includes radially extending flaps at each of said inflow end portion and said outflow end portion.

5. The stent of claim 2 in which said anchoring means includes radially extending flaps at each of said inflow end portion and said outflow end portion.

6. The stent of claim 2 in which said anchoring means includes multiple radially extending flaps at each of said inflow end portion and said outflow end portion.

7. The stent of claim 2 in which there are two rows of four equicircumferentially spaced radially extending flaps at said inflow end portion and one row of four equicircumferentially spaced radially extending flaps at said outflow end portion.

8. The stent of claim 1 wherein said drainage tube defines a continuously uninterrupted drainage lumen between said inflow end portion and said outflow end portion.

9. The stent of claim 2 wherein said drainage tube is defines a continuously uninterrupted drainage lumen between said inflow end portion and said outflow end portion.

*10. A stent for facilitating the drainage of fluids through an obstructed duct within the body, said stent comprising:*

*an inflow end portion, an outflow end portion, and a drainage tube therebetween, said inflow end portion defining inlet means for allowing fluid to enter into the inflow end of said drainage tube, said outflow end portion defining outlet means for allowing fluid to exit the outflow end of said drainage tube; and*

*means for anchoring said stent in an obstructed duct with the inflow end of said drainage tube positioned within the duct;*

*wherein said anchoring means comprise a plurality of radially extending flaps formed by slicing small longitudinal sections in said drainage tube and orienting said sliced sections radially, and wherein said sliced sections are made shallowly such that holes are not made in said drainage tube.*

*11. The stent of claim 10 wherein there are two rows of a first plurality of radially extending flaps at said inflow end portion and one row of a second plurality radially extending flaps at said outflow end portion.*

*12. The stent of claim 10 wherein there are two rows of four equicircumferentially spaced radially extending flaps at said inflow end portion and one row of four equicircumferentially spaced radially extending flaps at said outflow end portion.*

*13. A stent for facilitating the drainage of fluids through an obstructed duct within the body, said stent comprising:*

*an inflow end portion, an outflow end portion, and a drainage tube therebetween, said inflow end portion defining inlet means for allowing fluid to enter into the inflow end of said drainage tube, said outflow end portion defining outlet means for allowing fluid to exit the outflow end of said drainage tube; and*

*means for anchoring said stent in an obstructed duct with the inflow end of said drainage tube positioned within the duct;*

*wherein said anchoring means comprise a plurality of radially extending flaps formed by slicing small longitudinal sections in said drainage tube and orienting said sliced sections radially, and wherein said drainage tube defines a continuously uninterrupted drainage lumen between said inflow end portion and said outflow end portion.*

*14. A stent for facilitating the drainage of fluids through an obstructed duct within the body, said stent comprising:*

*an inflow end portion, an outflow end portion, and a drainage tube therebetween, said inflow end portion defining inlet means for allowing fluid to enter into the inflow end of said drainage tube, said outflow end portion defining outlet means for allowing fluid to exit the outflow end of said drainage tube; and*

*means for anchoring said stent in an obstructed duct with the inflow end of said drainage tube positioned within the duct;*

*wherein said anchoring means comprise two rows of a first plurality of radially extending flaps at said inflow end portion and one row of a second plurality of radially extending flaps at said outflow end portion, and wherein said flaps are formed by slicing small longitudinal sections in said drainage tube such that one end of each flap is severed from drainage tube.*

*15. The stent of claim 14 wherein said flaps are formed by orienting said sliced sections radially.*

*16. A stent for facilitating the drainage of fluids through an obstructed duct within the body, said stent comprising:*

*an inflow end portion, an outflow end portion, and a drainage tube therebetween, said inflow end portion defining inlet means for allowing fluid to enter into the inflow end of said drainage tube, said outflow end portion defining outlet means for allowing fluid to exit the outflow end of said drainage tube; and*

*means for anchoring said stent in an obstructed duct with the inflow end of said drainage tube positioned within the duct;*

*wherein said anchoring means comprise two rows of a first plurality of radially extending flaps at said inflow end portion and one row of a second plurality of radially extending flaps at said outflow end portion;*

*wherein said flaps are formed by a small longitudinal sections in said drainage tube and orienting said sliced sections radially, and wherein said sliced sections are made shallowly such that holes are not made in said drainage tube.*

*17. The stent of claim 14 wherein said first plurality of flaps comprise two rows of four equicircumferentially spaced flaps and said second plurality of flaps comprise one row of four equicircumferentially spaced flaps.*

*18. A stent for facilitating the drainage of fluids through an obstructed duct within the body, said stent comprising:*

*an inflow end portion, an outflow end portion, and a drainage tube therebetween, said inflow end portion defining inlet means for allowing fluid to enter into the inflow end of said drainage tube, said outflow end portion defining outlet means for allowing fluid to exit the outflow end of said drainage tube; and*

*means for anchoring said stent in an obstructed duct with the inflow end of said drainage tube positioned within the duct;*

*wherein said anchoring means comprise two rows of a first plurality of radially extending flaps at said inflow end portion and one row of a second plurality of radially extending flaps at said outflow end portion; and*

*wherein said drainage tube defines a continuously uninterrupted drainage lumen between said inflow end portion and said outflow end portion.*

* * * * *

UNITED STATES PATENT AND TRADEMARK OFFICE

CERTIFICATE OF CORRECTION

PATENT NO : Re. 35,849

DATED : July 14, 1998

INVENTOR(S) : Nib Soehendra

It is certified that error appears in the above-identified patent and that said Letters Patent is hereby corrected as shown below:

In column 6, line 21, please insert the word --said-- before the word "drainage".

In column 6, line 39, please delete the word "a" and insert in its place the word --slicing-- before the word "small".

Signed and Sealed this

Sixteenth Day of February, 1999

*Attest:*

*Attesting Officer*

*Acting Commissioner of Patents and Trademarks*